(12) United States Patent
Nagasaka et al.

(10) Patent No.: US 10,739,416 B2
(45) Date of Patent: Aug. 11, 2020

(54) GAS CELL, MAGNETIC FIELD MEASUREMENT DEVICE, AND METHOD FOR PRODUCING GAS CELL

(71) Applicant: SEIKO EPSON CORPORATION, Tokyo (JP)

(72) Inventors: Kimio Nagasaka, Hokuto (JP); Eiichi Fujii, Shiojiri (JP); Yasushi Tsuchiya, Fujimi-machi (JP)

(73) Assignee: SEIKO EPSON CORPORATION, Tokyo (JP)

( * ) Notice: Subject to any disclaimer, the term of this patent is extended or adjusted under 35 U.S.C. 154(b) by 282 days.

(21) Appl. No.: 15/810,990

(22) Filed: Nov. 13, 2017

(65) Prior Publication Data

US 2018/0143265 A1 May 24, 2018

(30) Foreign Application Priority Data

Nov. 22, 2016 (JP) ................................. 2016-226673

(51) Int. Cl.
| | | |
|---|---|---|
| *G01R 33/032* | (2006.01) | |
| *G01R 33/26* | (2006.01) | |
| *A61B 5/04* | (2006.01) | |
| *G01R 33/34* | (2006.01) | |
| *H01M 6/50* | (2006.01) | |

(52) U.S. Cl.
CPC ........ *G01R 33/032* (2013.01); *A61B 5/04005* (2013.01); *A61B 5/04007* (2013.01); *G01R 33/26* (2013.01); *G01R 33/34* (2013.01); *H01M 6/5038* (2013.01); *A61B 2562/12* (2013.01)

(58) Field of Classification Search
CPC ........ C07C 7/08; G01R 33/032; G01R 33/34; G01R 33/26
See application file for complete search history.

(56) References Cited

U.S. PATENT DOCUMENTS

| | | | | |
|---|---|---|---|---|
| 6,730,137 | B2 * | 5/2004 | Pesu ......................... | C10L 5/44 431/288 |
| 10,103,379 | B2 * | 10/2018 | Macklin ................ | H01M 4/131 |
| 2010/0232460 | A1 * | 9/2010 | Canham ................ | H01S 3/0387 372/25 |
| 2014/0349183 | A1 * | 11/2014 | Macklin ................ | H01M 4/386 429/213 |
| 2015/0369427 | A1 | 12/2015 | Nagasaka | |

FOREIGN PATENT DOCUMENTS

JP  2016-008836 A  1/2016

OTHER PUBLICATIONS

Alexandrov et al. (Physical Review A, vol. 66, 042903, 2002) (Year: 2002).*

(Continued)

*Primary Examiner* — Alesa Allgood
(74) *Attorney, Agent, or Firm* — Oliff PLC

(57) ABSTRACT

A gas cell includes a cell main body having a first chamber defined by an inner wall, and a first paraffin film provided on the inner wall, wherein in the first chamber, a gas which interacts with an electromagnetic wave is stored, the first paraffin film is a pure paraffin film, and a paraffin constituting the first paraffin film is arranged such that the directions of the molecular axes are aligned.

12 Claims, 12 Drawing Sheets

(56) References Cited

OTHER PUBLICATIONS

Franzen, W., "Spin Relaxation of Optically Aligned Rubidium Vapor," Physical Review, vol. 115, No. 4, pp. 850-856 (Aug. 15, 1959).

Singh et al.; "A Technique for Preparing Wall Coated Cesium Vapor Cells;" The Review of Scientific Instruments; 1388-1389; 1972; vol. 43, No. 9.

Wu et al.; "Surface Freezing in Binary Mixtures of Alkanes: New Phases and Phase Transitions;" Phys. Rev. Lett., 1332-1335; 1995; vol. 75, No. 7.

\* cited by examiner

GAS CELL, MAGNETIC FIELD MEASUREMENT DEVICE, AND METHOD FOR PRODUCING GAS CELL

BACKGROUND

1. Technical Field

The present invention relates to a gas cell, a magnetic field measurement device, and a method for producing a gas cell.

2. Related Art

As a magnetic field measurement device which detects a magnetic field emitted from the heart or the like of a living body, there is known an optically pumped type magnetic field measurement device. In the optically pumped type magnetic field measurement device, a gas cell having an alkali metal gas enclosed therein is irradiated with a linearly polarized light, and a magnetic field is measured according to the rotating angle of a polarization plane of the light transmitted through the gas cell.

In the magnetic field measurement device, an alkali metal in the gas cell is spin-polarized by the light, and thereafter collides with the inner wall of the gas cell and returns to a thermal equilibrium state (the spin polarization is relaxed). When a time until the alkali metal returns to a thermal equilibrium state becomes longer, the performance is improved. There is known a technique in which in order to suppress relaxation of alkali metal spin polarization, the inner wall of the gas cell is coated with a paraffin film (see JP-A-2016-8836 (Patent Document 1). In this manner, it is important for the magnetic field measurement device to suppress relaxation of alkali metal spin polarization.

SUMMARY

An advantage of some aspects of the invention is to provide a gas cell capable of suppressing relaxation of spin polarization. Another advantage of some aspects of the invention is to provide a magnetic field measurement device including the gas cell. Still another advantage of some aspects of the invention is to provide a method for producing a gas cell capable of suppressing relaxation of spin polarization.

A gas cell according to an aspect of the invention includes a cell main body having a first chamber defined by an inner wall, and a first paraffin film provided on the inner wall, wherein in the first chamber, a gas which interacts with an electromagnetic wave is stored, the first paraffin film is a pure paraffin film, and a paraffin constituting the first paraffin film is arranged such that the directions of the molecular axes are aligned.

According to such a gas cell, as compared with the case where the paraffin is not arranged such that the directions of the molecular axes are aligned, the crystallinity of the first paraffin film is high, and therefore, the first paraffin film can have a dense and smooth surface, and relaxation of spin polarization can be suppressed.

A gas cell according to an aspect of the invention includes a cell main body having a first chamber defined by an inner wall, and a first paraffin film provided on the inner wall, wherein in the first chamber, a gas which interacts with an electromagnetic wave is stored, the first paraffin film is a mixed pure paraffin film, and a paraffin constituting the first paraffin film is arranged such that the directions of the molecular axes are aligned.

According to such a gas cell, as compared with the case where the paraffin is not arranged such that the directions of the molecular axes are aligned, the crystallinity of the first paraffin film is high, and therefore, the first paraffin film can have a dense and smooth surface and relaxation of spin polarization can be suppressed.

In the gas cell according to the aspect of the invention, the paraffin film may be a mixed pure paraffin film of a first paraffin and a second paraffin having a different carbon number from the first paraffin.

According to such a gas cell, relaxation of spin polarization can be suppressed.

In the gas cell according to the aspect of the invention, the paraffin film may be a mixed pure paraffin film of a paraffin having a carbon number of 50 and a paraffin having a carbon number of 38.

According to such a gas cell, relaxation of spin polarization can be more reliably suppressed (see "5. Experimental Examples" for the details).

In the gas cell according to the aspect of the invention, a second paraffin film provided between the inner wall and the first paraffin film may be included, and the second paraffin film may have a lower melting point than the first paraffin film.

According to such a gas cell, the first paraffin film and the second paraffin film are formed by utilizing surface freezing (SF), and a paraffin constituting the first paraffin film can be arranged such that the directions of the molecular axes are aligned.

In the gas cell according to the aspect of the invention, the gas which interacts with an electromagnetic wave may be a gas of an alkali metal.

According to such a gas cell, relaxation of spin polarization can be suppressed.

In the gas cell according to the aspect of the invention, the cell main body may have a second chamber which communicates with the first chamber through a communication hole.

According to such a gas cell, the vapor pressure of the alkali metal in a gaseous state in the first chamber can be adjusted, and also the amount of the alkali metal in a gaseous state in the first chamber can be adjusted.

A magnetic field measurement device according to an aspect of the invention includes the gas cell according to the aspect of the invention.

According to such a magnetic field measurement device, the gas cell according to the aspect of the invention is included, and therefore, relaxation of spin polarization can be suppressed.

A method for producing a gas cell according to an aspect of the invention includes a paraffin placing step of placing a paraffin in an internal space of a cell main body, a heating step of heating the cell main body to vaporize the paraffin, a first cooling step of cooling the cell main body after the heating step to cool the paraffin to a first temperature higher than the surface freezing temperature, a second cooling step of cooling the cell main body after the first cooling step to cool the paraffin to a second temperature lower than the melting point of the paraffin, and a filling step of filling an alkali metal in a gaseous state in the internal space of the cell main body, wherein the average temperature lowering rate in the second cooling step is 1° C./hour or more and 10° C./hour or less.

According to such a method for producing a gas cell, the second cooling step in which surface freezing occurs can be performed by taking time, and a paraffin film composed of a paraffin which is arranged such that the directions of the molecular axes are aligned can be formed. Therefore, in such a method for producing a gas cell, a gas cell capable of suppressing relaxation of spin polarization can be produced.

In the method for producing a gas cell according to the aspect of the invention, after the second cooling step and before the filling step, a maintaining step of maintaining the paraffin at the second temperature may be included.

According to such a method for producing a gas cell, a paraffin film having stable properties can be formed.

In the method for producing a gas cell according to the aspect of the invention, a paraffin film formed in the heating step, the first cooling step, and the second cooling step may be a mixed pure paraffin film.

According to such a method for producing a gas cell, a difference between the surface freezing temperature of the paraffin and the bulk melting point of the paraffin can be made larger than in the case where a pure paraffin film is formed, and the second cooling step in which surface freezing occurs can be performed by taking time.

In the method for producing a gas cell according to the aspect of the invention, an alkali metal placing step of placing a vessel having the alkali metal stored therein in the internal space may be included, and in the filling step, the alkali metal in a gaseous state may be filled in the internal space by destroying the vessel.

According to such a method for producing a gas cell, in the filling step, the alkali metal in a gaseous state can be filled in the first chamber in a state where air tightness of the internal space is maintained.

In the method for producing a gas cell according to the aspect of the invention, an alkali metal placing step of placing a solid material containing the alkali metal in the internal space may be included, and in the filling step, the alkali metal in a gaseous state may be filled in the internal space by irradiating the solid material with a laser beam.

According to such a method for producing a gas cell, the alkali metal gas can be filled in the first chamber without placing a vessel having the alkali metal stored therein in the internal space.

In the method for producing a gas cell according to the aspect of the invention, the average temperature lowering rate in the second cooling step may be slower than the average temperature lowering rate in the first cooling step.

According to such a method for producing a gas cell, the second cooling step in which surface freezing occurs can be performed by taking time.

BRIEF DESCRIPTION OF THE DRAWINGS

The invention will be described with reference to the accompanying drawings, wherein like numbers reference like elements.

DESCRIPTION OF EXEMPLARY EMBODIMENTS

Hereinafter, preferred embodiments of the invention will be described in detail with reference to the drawings. Note that the embodiments described below are not intended to unduly limit the content of the invention described in the appended claims. Further, all the configurations described below are not necessarily essential components of the invention.

1. MAGNETIC FIELD MEASUREMENT DEVICE

Figure 1:
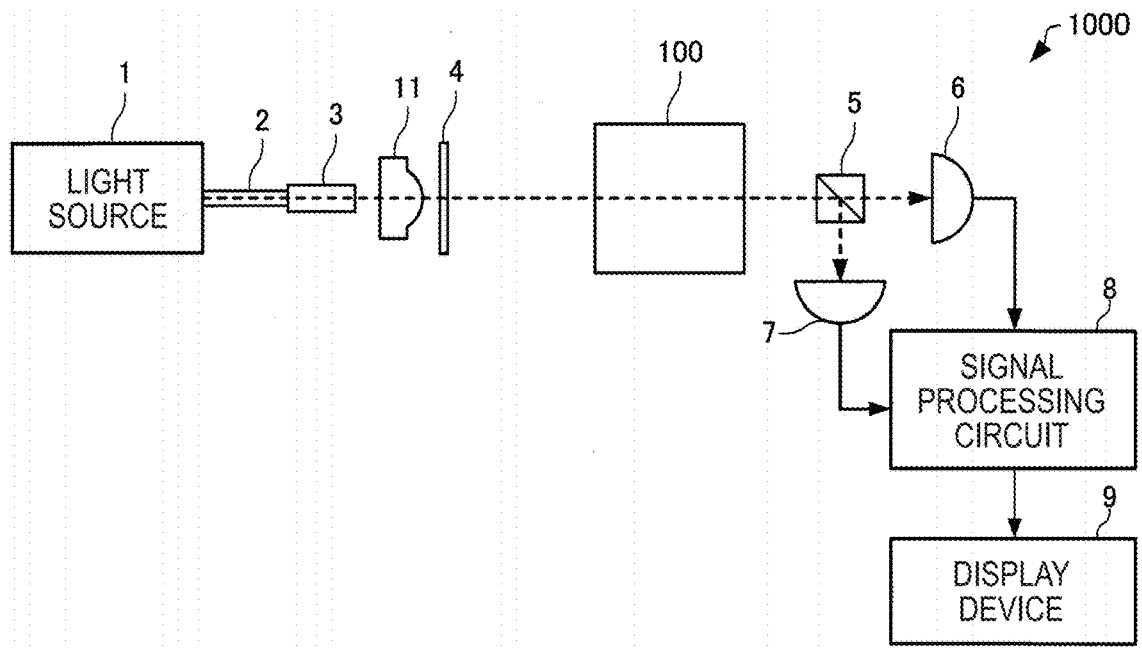
FIG. 1 is a block diagram showing a configuration of a magnetic field measurement device according to an embodiment.

First, a magnetic field measurement device according to this embodiment will be described with reference to the drawings. FIG. 1 is a block diagram showing a configuration of a magnetic field measurement device 1000 according to this embodiment.

The magnetic field measurement device 1000 is a magnetic field measurement device using a nonlinear magneto-optical rotation (NMOR). The magnetic field measurement device 1000 is used in, for example, a living body state measurement device (a magnetocardiograph, a magnetoencephalograph, or the like) which measures a weak magnetic field emitted from a living body such as a magnetic field from the heart (cardiac magnetism) or a magnetic field from the brain (cerebral magnetism). The magnetic field measurement device 1000 can also be used in a metal detector or the like.

The magnetic field measurement device 1000 includes a gas cell according to the invention. Hereinafter, an example using a gas cell 100 as the gas cell according to the invention will be described.

The magnetic field measurement device 1000 is configured to include a light source 1, an optical fiber 2, a connector 3, a polarizing plate 4, a gas cell 100, a polarization splitter 5, a photodetector (PD) 6, a photodetector (PD) 7, a signal processing circuit 8, and a display device 9. In the gas cell 100, an alkali metal gas (an alkali metal in a gaseous state) is stored. As the alkali metal, for example, cesium (Cs), rubidium (Rb), potassium (K), sodium (Na), or the like can be used. In the following description, a case where cesium is used as the alkali metal will be described as an example.

The light source 1 is a device which outputs a laser beam having a wavelength corresponding to a cesium absorption line (for example, 894 nm corresponding to the D1 line), for example, a tunable laser. The laser beam output from the light source 1 is a so-called continuous wave (CW) light having a continuously constant light intensity.

The optical fiber 2 is a member which guides the laser beam output from the light source 1 to the gas cell 100 side. As the optical fiber 2, for example, a polarization-maintaining fiber or a single-mode optical fiber which propagates only a basic mode is used.

The connector 3 is a member connected to the optical fiber 2. The connector 3 is, for example, connected to the optical fiber 2 in a screwed manner.

A collimator lens 11 is a lens for converting the laser beam into a parallel light.

The polarizing plate 4 is an element which polarizes the laser beam in a specific direction into a linearly polarized light.

Figure 2:
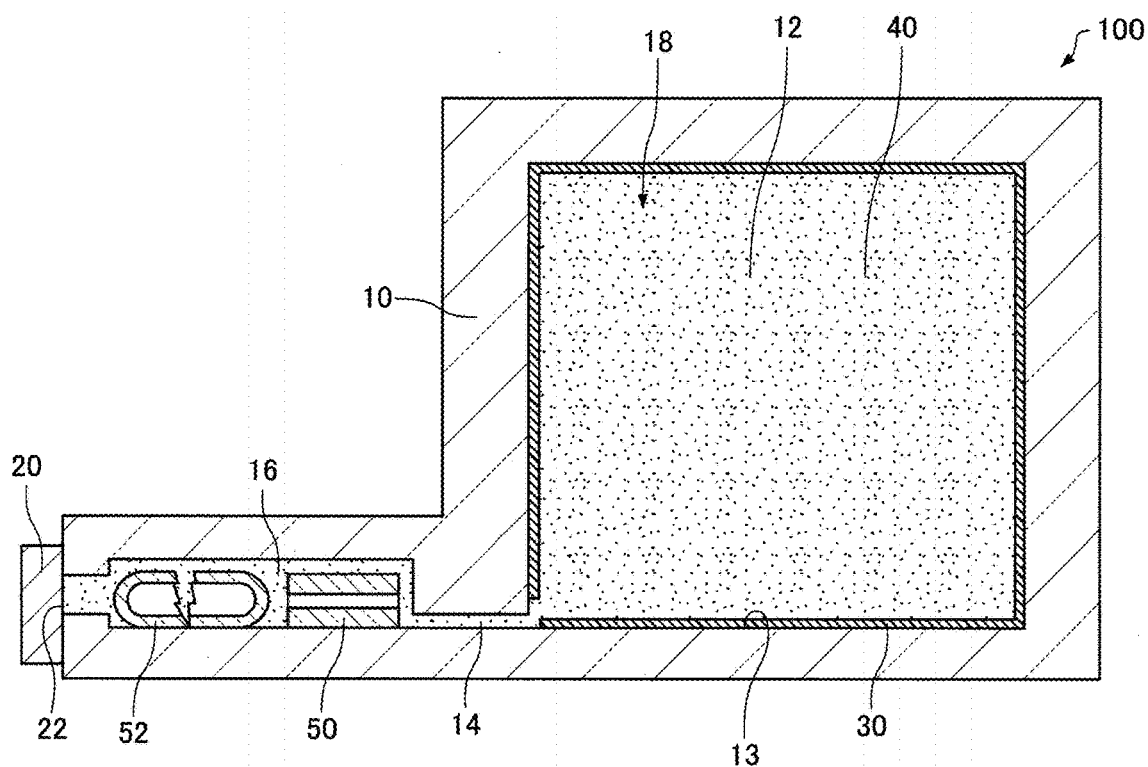
FIG. 2 is a cross-sectional view schematically showing a gas cell according to an embodiment.

The gas cell 100 is a box (cell) having a void therein, and the alkali metal in a gaseous state (the vapor of the alkali metal) is stored in the void (a first chamber 12 shown in FIG. 2). The configuration of the gas cell 100 will be described later.

The polarization splitter 5 is an element which splits the incident laser beam into beams having two polarization components that are orthogonal to each other. The polarization splitter 5 is, for example, a Wollaston prism or a polarizing beam splitter.

The photodetector 6 and the photodetector 7 are detectors having sensitivity to the wavelength of the laser beam, and output an electric current corresponding to the light intensity of the incident light to the signal processing circuit 8. If the photodetector 6 and the photodetector 7 generate a magnetic field by themselves, there is a possibility that the measurement may be affected. Therefore, the photodetector 6 and the photodetector 7 are preferably constituted by a non-magnetic material. The photodetector 6 and the photodetector 7 are placed on the same side as the polarization splitter 5 when viewed from the gas cell 100 (downstream side).

In the magnetic field measurement device 1000, the light source 1 is located on the most upstream side of the path of the laser beam, and on the downstream side of the light source 1, the optical fiber 2, the connector 3, the polarizing plate 4, the gas cell 100, the polarization splitter 5, and the photodetectors 6 and 7 are arranged in this order from the upstream side to the downstream side.

The operations of the respective sections in the magnetic field measurement device 1000 will be described.

The laser beam output from the light source 1 is guided to the optical fiber 2 and reaches the polarizing plate 4. The laser beam is converted into a linearly polarized light having a higher polarization degree by the polarizing plate 4. In the gas cell 100, the laser beam excites (optically pumps) alkali metal atoms enclosed in the gas cell 100. At this time, the laser beam is subjected to a polarization plane rotation action according to the intensity of a magnetic field so that the polarization plane is rotated. The laser beam transmitted through the gas cell 100 is split into beams having two polarization components by the polarization splitter 5. The light intensities of the beams having two polarization components are measured (probed) by the photodetector 6 and the photodetector 7, respectively.

The signal processing circuit 8 receives signals indicating the light intensities of the beams measured by the photodetector 6 and the photodetector 7, respectively. The signal processing circuit 8 determines the rotation angle of the polarization plane of the laser beam on the basis of each of the received signals. The simplest method is to obtain a difference between both signals. The signal processing circuit 8 determines the intensity of the magnetic field in the propagation direction of the laser beam from the rotation angle of the polarization plane. The display device 9 displays the intensity of the magnetic field determined by the signal processing circuit 8.

2. GAS CELL

Next, the gas cell according to this embodiment will be described with reference to the drawings. FIG. 2 is a cross-sectional view schematically showing the gas cell 100 according to this embodiment.

As shown in FIG. 2, the gas cell 100 includes a cell main body 10, a sealing plug 20, and a coating film 30.

The material of the cell main body 10 is desirably borosilicate glass or quartz glass which has excellent heat resistance, transmits an absorption line of the alkali metal gas, and has low absorption in an ultraviolet region. The cell main body 10 can be formed by, for example, bonding quartz plates to one another. The thickness of the quartz plates constituting the cell main body 10 is, for example, 0.5 mm or more and 5 mm or less.

The cell main body 10 has a first chamber (main chamber) 12, a communication hole (capillary) 14, and a second chamber (sub-chamber or reservoir) 16.

The first chamber 12 is defined by an inner wall 13 of the cell main body 10. In the first chamber 12, an alkali metal gas (a gas of an alkali metal) 40 is stored. The alkali metal gas is a gas which interacts with an electromagnetic wave. In the example shown in the drawing, in the first chamber 12, the alkali metal gas 40 is filled (packed). By irradiating the first chamber 12 with a light (laser beam), the alkali metal interacts with the light to cause spin polarization, quantum interference, or the like due to optical pumping. The gas stored in the first chamber 12 is not limited to the alkali metal gas as long as it is a gas which interacts with an electromagnetic wave, and may be, for example, a gas of strontium (Sr), magnesium (Mg), calcium (Ca), barium (Ba), or the like.

The communication hole 14 connects the first chamber 12 and the second chamber 16 to each other. The communication hole 14 is formed so that the alkali metal gas 40 can pass therethrough. The communication hole 14 is formed in such a size that the proportion of the alkali metal gas 40 stored in the first chamber 12 returning from the first chamber 12 to the second chamber 16 becomes small. The cross-sectional area of the communication hole 14 (the cross-sectional area cut in a direction orthogonal to a direction directed from the first chamber 12 to the second chamber 16) is, for example, about one-several thousandth of the cross-sectional area of the first chamber 12.

The second chamber 16 communicates with the first chamber 12 through the communication hole 14. The first chamber 12, the communication hole 14, and the second chamber 16 constitute an internal space 18 of the cell main body 10. The internal space 18 is made airtight so as to prevent a gas from going to or coming from the outside.

The volume of the second chamber 16 is, for example, smaller than the volume of the first chamber 12. In the second chamber 16, a first vessel 50 having a paraffin stored therein and a second vessel 52 having the alkali metal stored therein are housed. By vaporizing the paraffin stored in the first vessel 50, the coating film 30 can be formed on the inner wall 13 which defines the first chamber 12. By vaporizing the alkali metal stored in the second vessel 52, the alkali metal gas can be filled in the first chamber 12. In the second chamber 16, the alkali metal is stored in a solid or liquid state.

The sealing plug 20 seals an input port 22. By doing this, the internal space 18 can be made airtight. The input port 22 is an inlet for introducing the first vessel 50 and the second vessel 52 into the second chamber 16 from the outside. The material of the sealing plug 20 is, for example, quartz glass. The material of the sealing plug 20 may be the same as the material of the cell main body 10. The sealing plug 20 is joined to the cell main body 10 using a low-melting point glass powder (glass frit).

The coating film 30 is provided on the inner wall 13 of the cell main body 10 which defines the first chamber 12. The coating film 30 covers the inner wall 13 with a coverage of, for example, 95% or more, preferably 99% or more, more preferably 99.9% or more. Although not shown in the drawing, the coating film 30 may be provided on the inner wall of the cell main body 10 which defines the communication hole 14, or may be provided on the inner wall of the cell main body 10 which defines the second chamber 16.

The material of the coating film 30 is a paraffin. The paraffin is an alkane having a carbon number of 20 or more (a chain saturated hydrocarbon with a general formula of $C_nH_{2n+2}$). The paraffin constituting the coating film 30 has, for example, a linear molecular structure with no branch. The carbon number of the paraffin constituting the coating film 30 is, for example, 20 or more and 100 or less, preferably 30 or more and 60 or less. The carbon number (molecular weight) of the paraffin constituting the coating film 30 can be measured by, for example, gas chromatography.

The coating film 30 has a paraffin film (a second paraffin film) 32 and a paraffin film (a first paraffin film) 34. The paraffin film 32 is provided on the surface of the inner wall 13 (on the inner wall 13). The paraffin film 34 is provided on the inner wall 13 through the paraffin film 32. The paraffin film 34 is provided on the surface of the paraffin film 32 (on the paraffin film 32).

The coating film 30 (paraffin films 32 and 34) may be, for example, a pure paraffin film. The pure paraffin film is a film constituted by paraffins having the same molecular weight (carbon number) in an amount of 98% or more of the paraffins constituting the paraffin film, and is preferably a film in which all paraffins constituting the paraffin film have the same molecular weight. By removing paraffins having different molecular weights through fractional distillation, a pure paraffin film can be formed. Paraffins having various molecular weights are obtained merely by performing fractional distillation.

The coating film 30 (paraffin films 32 and 34) may be, for example, a mixed pure paraffin film. The mixed pure paraffin film is a film formed by mixing a plurality of pure paraffin raw materials. A pure paraffin raw material is constituted by paraffins (main paraffins) having the same molecular weight in an amount of 98% or more, and a mixed pure paraffin film is formed by mixing a plurality of pure paraffin raw materials in which the main paraffins have different molecular weights. It is preferred that all paraffins constituting the pure paraffin raw material have the same molecular weight. The mixed pure paraffin film may be formed by mixing two types of pure paraffin raw materials, or may be formed by mixing three or more types of pure paraffin raw materials.

The coating film 30 (paraffin films 32 and 34) may be, for example, a mixed pure paraffin film of a paraffin having a carbon number of 50 (a first paraffin) and a paraffin having a carbon number of 38 (a second paraffin having a different carbon number from the first paraffin). That is, each of the paraffin films 32 and 34 may be a mixed pure paraffin film formed by mixing a first pure paraffin raw material containing a paraffin having a carbon number of 50 as the main paraffin, and a second pure paraffin raw material containing a paraffin having a carbon number of 38 as the main paraffin. The mixing ratio of the first pure paraffin raw material to the second pure paraffin raw material is not particularly limited. Each of the paraffin films 32 and 34 may be a mixed pure paraffin film composed of only a paraffin having a carbon number of 50 and a paraffin having a carbon number of 38.

Figure 3:
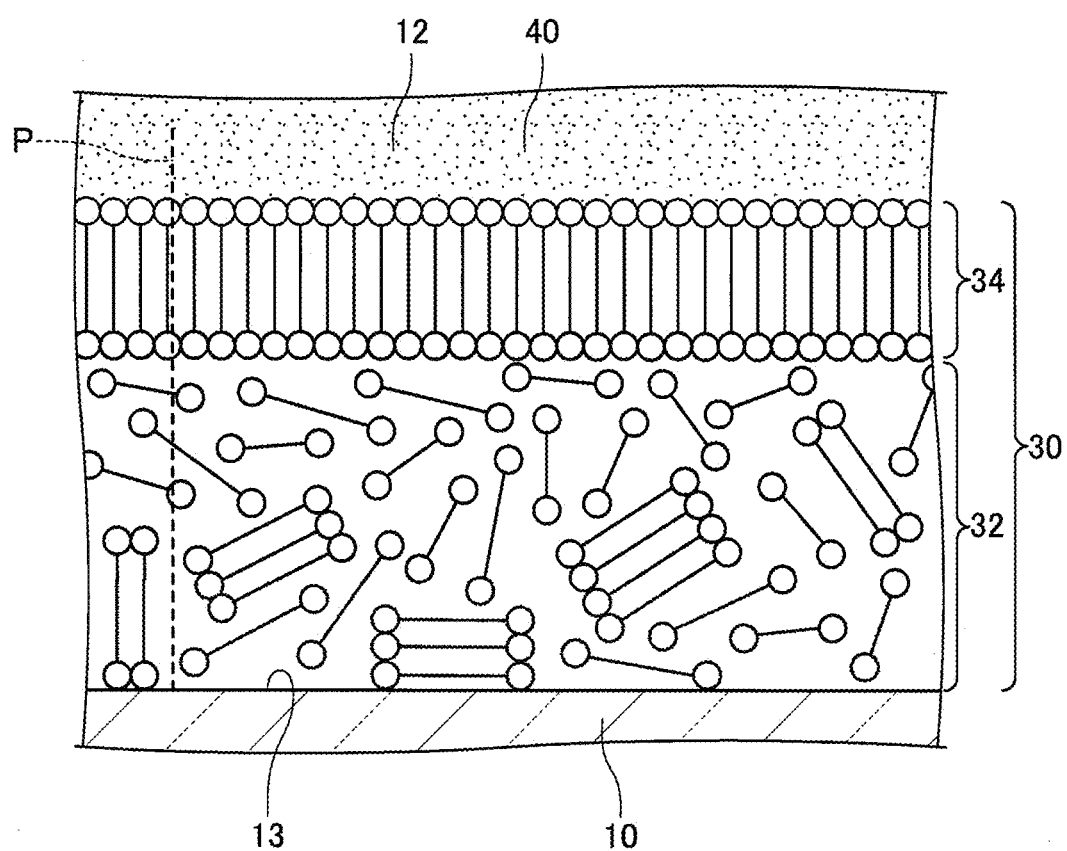
FIG. 3 is a view for illustrating a paraffin film according to an embodiment.

Here, FIG. 3 is an enlarged view in the vicinity of the coating film 30 shown in FIG. 2, and is a view for illustrating the coating film 30. For convenience sake, in FIG. 3, a methyl group ($—CH_3$) at both ends of a paraffin (paraffin molecule) is indicated by a circle (○), and a linear portion therebetween (an alkyl chain: $—(CH_2)_n—$) is indicated by a segment. Further, in FIG. 3, a case where the coating film 30 is a mixed pure paraffin film is shown as one example, and the length of the segment reflects a molecular length.

The thickness of the paraffin film 32 is, for example, 1 nm or more and 50 nm or less. The paraffin film 32 has a lower crystallinity than the paraffin film 34. The paraffin film 32 may be amorphous or may have crystallinity. When the paraffin film 32 has crystallinity, the paraffin film 32 has a lower crystallinity than the paraffin film 34. In the case where the paraffin film 32 is a mixed pure paraffin film, the paraffin film 32 may be eutectic. The paraffin constituting the paraffin film 32 is configured such that the directions in the longitudinal directions of the alkyl chains (linear portions) (the directions of the molecular axes) of the paraffin are less aligned than the paraffin constituting the paraffin film 34. Further, in the case where the total amount of the paraffin is small, the paraffin film 32 may not be formed.

The thickness of the paraffin film 34 is, for example, 2 nm or more and 20 nm or less. The paraffin film 34 has a higher crystallinity than the paraffin film 32. The paraffin film 34 may be a single crystal. In the case where the paraffin film 34 is a mixed pure paraffin film, the paraffin film 34 may be eutectic. In the case where the paraffin film 34 is a mixed pure paraffin film, the composition of the paraffins constituting the paraffin film 32 and the composition of the paraffins constituting the paraffin film 34 may be different from each other.

The paraffin constituting the paraffin film 34 is arranged such that the directions in the longitudinal directions of the alkyl chains (the directions of the molecular axes) are aligned. In the example shown in the drawing, the longitudinal direction of the alkyl chain of the paraffin is parallel to the vertical line P of the inner wall 13. Although not shown in the drawing, the longitudinal direction of the alkyl chain may be tilted with respect to the vertical line P at an angle of 45° or less, or may be tilted at an angle of 20° or less. The paraffin constituting the paraffin film 34 is, for example, arranged in a direction orthogonal to the extending direction of the vertical line P. In the example shown in the drawing, the lengths of the alkyl chains of the paraffin constituting the paraffin film 34 are equal to one another, however, in the case where the coating film 30 is a mixed pure paraffin film, the lengths of the alkyl chains of the paraffins constituting the paraffin film 34 may be different from one another.

The melting point of the paraffin film 34 is higher than the melting point of the paraffin film 32. That is, the melting point of the paraffin film 32 is lower than the melting point of the paraffin film 34. The melting points of the paraffin film 32 and the paraffin film 34 are, for example, 50° C. or higher and 120° C. or lower, and the difference between the melting point of the paraffin film 34 and the melting point of the paraffin film 32 is, for example, 2° C. or more and 20° C. or less. It can be confirmed that the melting point of the paraffin film 34 is higher than the melting point of the paraffin film 32, for example, by the fact that when the coating film 30 is heated, the paraffin film 32 starts to melt faster than the paraffin film 34.

The gas cell 100 has, for example, the following features.

In the gas cell 100, the paraffin constituting the paraffin film 34 is arranged such that the directions of the molecular axes are aligned. According to this, in the gas cell 100, as compared with the case where the paraffin is not arranged such that the directions of the molecular axes are aligned, the crystallinity of the paraffin film 34 is high, and therefore, the paraffin film 34 can have a dense and smooth surface and relaxation of spin polarization can be suppressed.

Further, in the gas cell 100, the paraffin film 34 may be a pure paraffin film. According to this, in the gas cell 100, the properties (for example, the property of relaxation of spin polarization) of the paraffin film 34 is stable as compared with the case where the paraffin film is not a pure paraffin film, but is constituted by paraffins having various molecular weights.

Further, in the gas cell 100, the paraffin film 34 may be a mixed pure paraffin film. According to this, in the gas cell 100, relaxation of spin polarization can be further suppressed as compared with the case where the paraffin film is a pure paraffin film (see "5. Experimental Examples" for the details).

Further, in the gas cell 100, the paraffin film 34 may be a mixed pure paraffin film of a paraffin having a carbon number of 50 and a paraffin having a carbon number of 38. According to this, in the gas cell 100, relaxation of spin polarization can be more reliably suppressed (see "5. Experimental Examples" for the details).

In the gas cell 100, the paraffin film 32 provided between the inner wall 13 and the paraffin film 34 is included, and the paraffin film 32 has a lower melting point than the paraffin film 34. According to this, in the gas cell 100, the paraffin films 32 and 34 are formed by utilizing surface freezing (SF), and the paraffin constituting the paraffin film 34 can be arranged such that the directions of the molecular axes are aligned. Further, in the gas cell 100, the paraffin films 32 and 34 are formed by utilizing SF, and therefore, the paraffin films 32 and 34 have high adhesion and coverage. The SF will be described later.

In the gas cell 100, the cell main body 10 may have the second chamber 16 which communicates with the first chamber 12 through the communication hole 14. According to this, in the gas cell 100, since the alkali metal in a solid or liquid state is stored in the second chamber 16, the vapor pressure of the alkali metal gas 40 in the first chamber 12 can be adjusted by vaporizing or liquefying the alkali metal in the second chamber 16 in the case where the pressure of the alkali metal gas 40 in the first chamber 12 deviates from the saturated vapor pressure determined by the temperature. Further, the alkali metal gas 40 diffuses in the cell main body 10 or reacts with an impurity or the like leaking from the outside to cause oxidation or hydroxylation, though to a small extent, and so on, and therefore, the alkali metal is reduced after a long run in some cases. In such a case, by the alkali metal stored in the second chamber 16, the amount of the alkali metal gas 40 in the first chamber 12 can be adjusted. In this manner, the second chamber 16 can play a role in storing the alkali metal.

3. METHOD FOR PRODUCING GAS CELL

Figure 4:
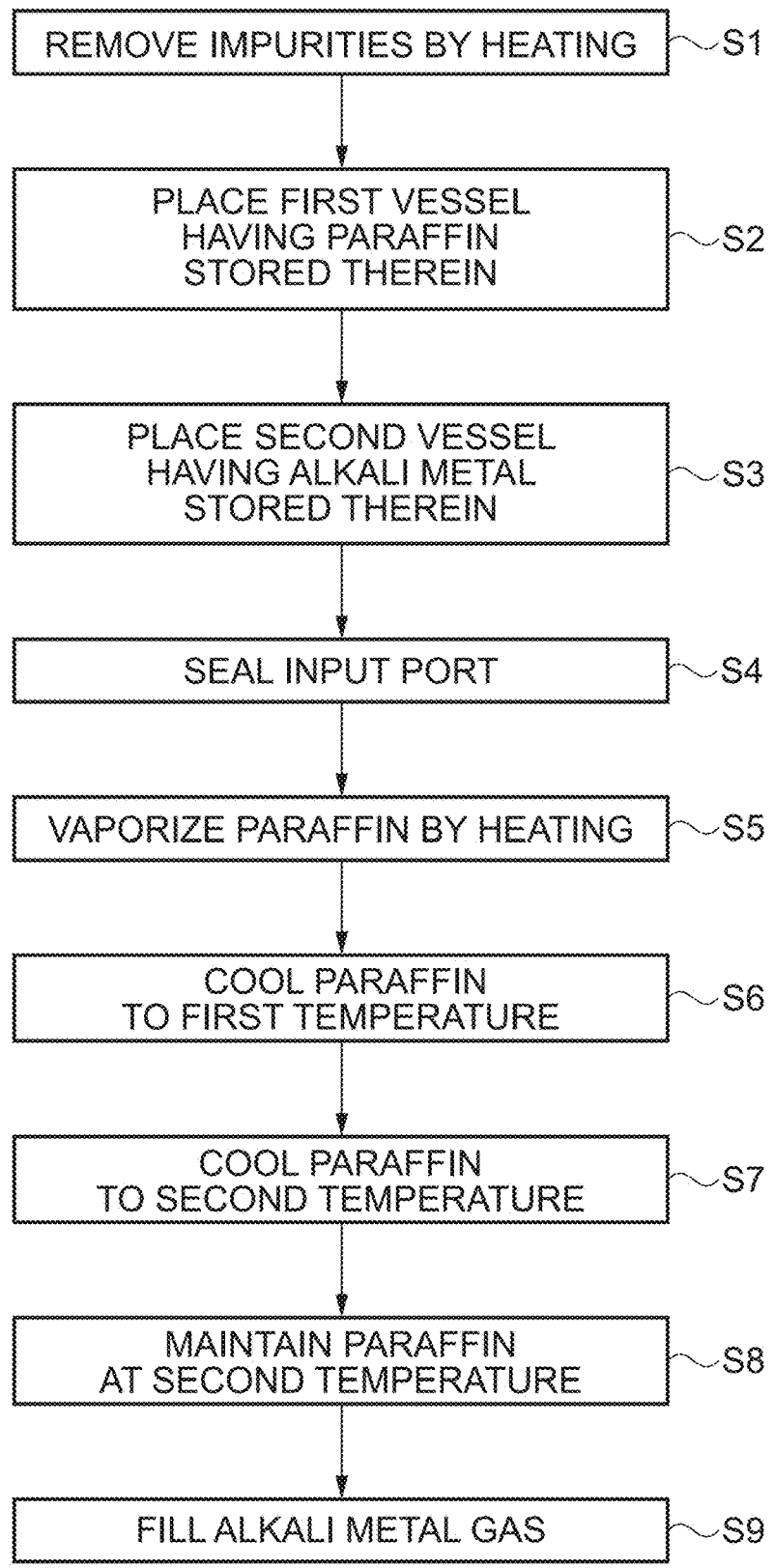
FIG. 4 is a flowchart for illustrating a method for producing a gas cell according to an embodiment.

Next, a method for producing a gas cell according to this embodiment will be described with reference to the drawings. FIG. 4 is a flowchart for illustrating a method for producing the gas cell 100 according to this embodiment. FIG. 5 to FIG. 9 are cross-sectional views schematically showing the method for producing the gas cell 100 according to this embodiment.

Figure 5:
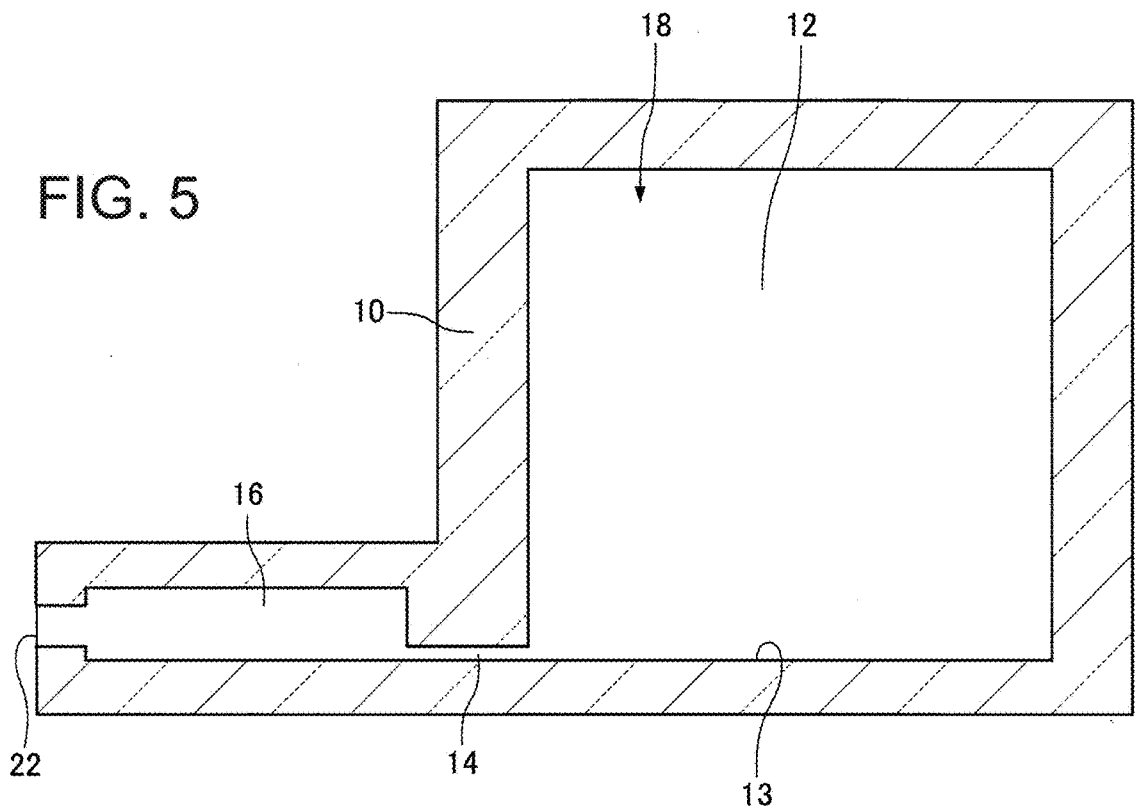
FIG. 5 is a cross-sectional view schematically showing the method for producing a gas cell according to the embodiment.

As shown in FIG. 5, a cell main body 10 is prepared, and impurities adhered to an inner wall 13 of the cell main body 10 is removed by heating the cell main body 10 in a reduced pressure state (Step S1). In this step, for example, the cell main body 10 is placed on an oven (not shown) and heated to 300° C. or higher and 600° C. or lower.

Figure 6:
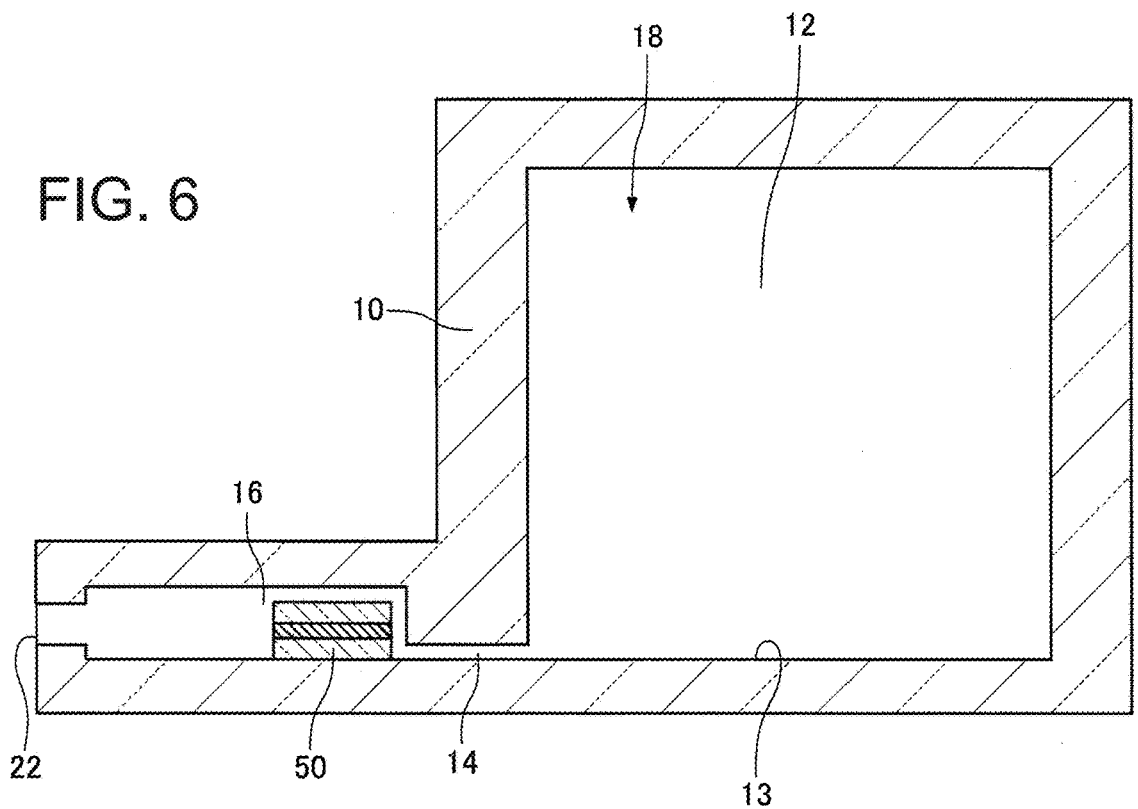
FIG. 6 is a cross-sectional view schematically showing the method for producing a gas cell according to the embodiment.

As shown in FIG. 6, a first vessel 50 having a paraffin stored therein is placed in a second chamber 16 of the cell main body 10 through an input port 22 (Step S2, a paraffin placing step). This step is performed, for example, at room temperature in a nitrogen atmosphere. The filling of the paraffin in the first vessel 50 is performed, for example, as follows. The paraffin in a solid or powder state is prepared, and melted by heating the paraffin under a reduced pressure to homogenize the paraffin, and then, the melted paraffin is filled in the first vessel 50 by utilizing a capillary phenomenon. The first vessel 50 is, for example, a tubular glass tube. In the case where a mixed paraffin film is formed, a plurality of types of raw materials are weighed and mixed at a predetermined mixing ratio, and the resulting material is filled in the first vessel 50. The first vessels 50 having the paraffin stored therein are placed as many as needed for the formation of a coating film 30.

Figure 7:
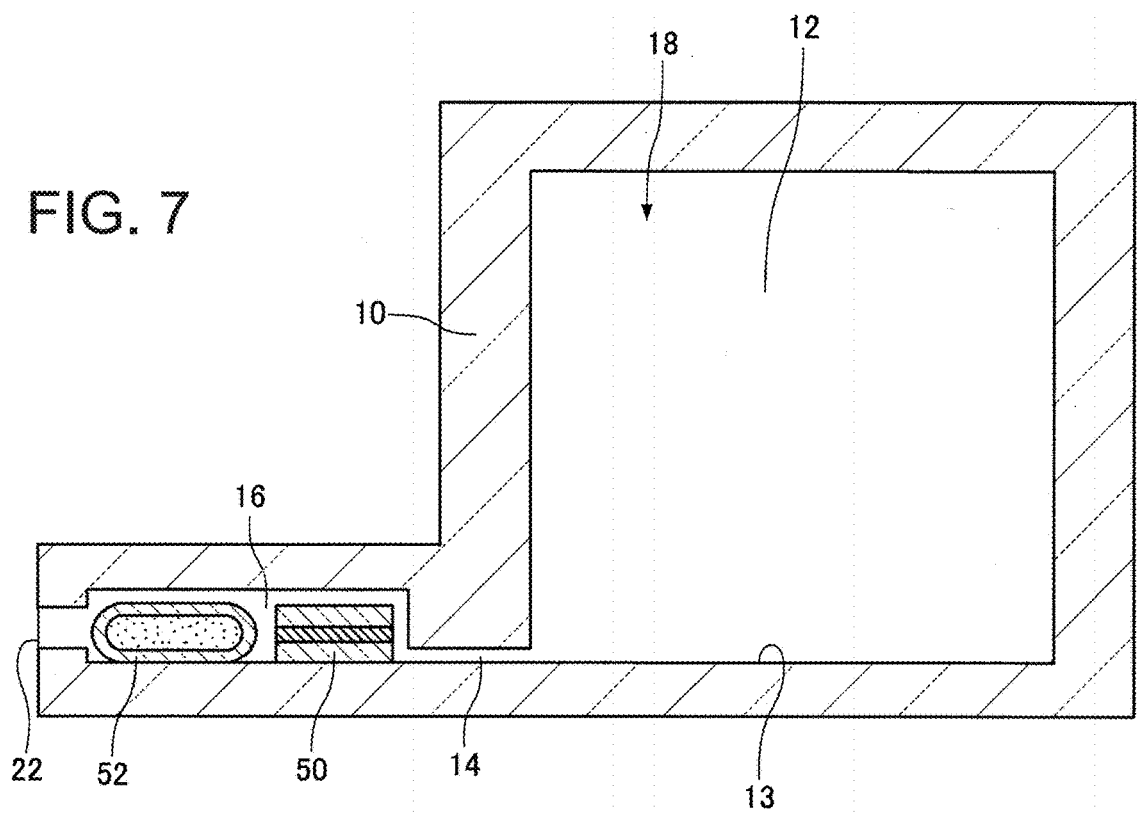
FIG. 7 is a cross-sectional view schematically showing the method for producing a gas cell according to the embodiment.

As shown in FIG. 7, a second vessel 52 having an alkali metal stored therein is placed in a second chamber 16 of the cell main body 10 through an input port 22 (Step S3, an alkali metal placing step). This step is performed, for example, at room temperature in a nitrogen atmosphere. The second vessel 52 having the alkali metal stored therein is obtained by, for example, filling the alkali metal inside a tubular glass tube in a vacuum state, and sealing both ends of the glass tube by welding. The second vessels 52 having the alkali metal stored therein are prepared as many as needed for the filling of a predetermined amount of an alkali metal gas 40 in the first chamber 12. The order of the paraffin placing step (Step 2) and the alkali metal placing step (Step S3) may be changed.

Figure 8:
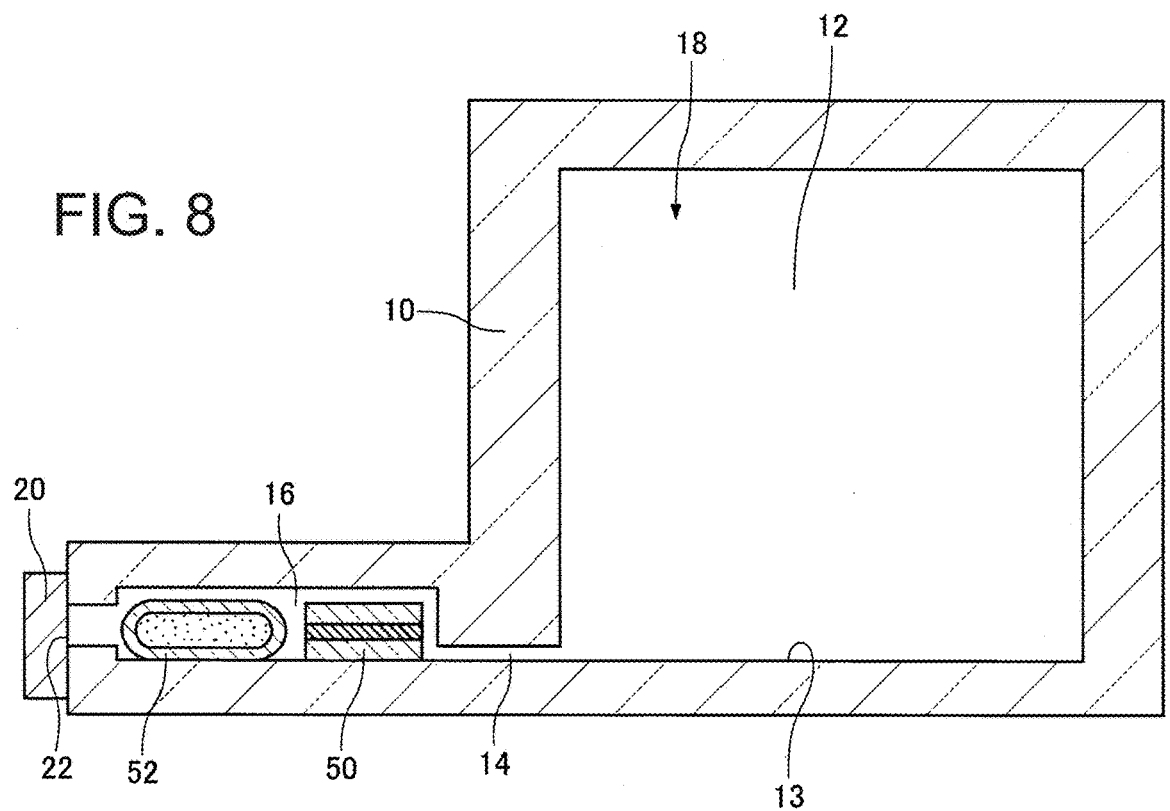
FIG. 8 is a cross-sectional view schematically showing the method for producing a gas cell according to the embodiment.

As shown in FIG. 8, the input port 22 is sealed with a sealing plug 20 in a reduced pressure state (Step S4). By doing this, the internal space 18 of the cell main body 10 can be brought into a vacuum state.

Figure 9:
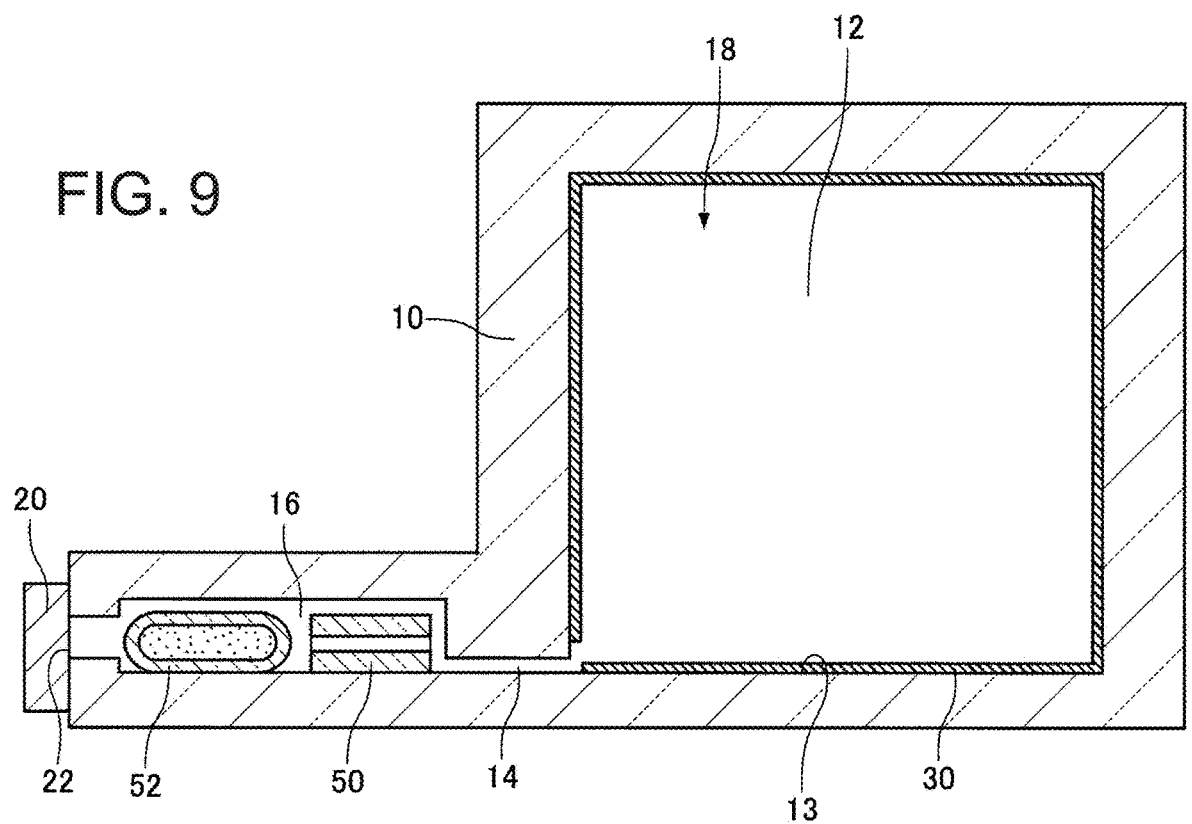
FIG. 9 is a cross-sectional view schematically showing the method for producing a gas cell according to the embodiment.
Figure 10:
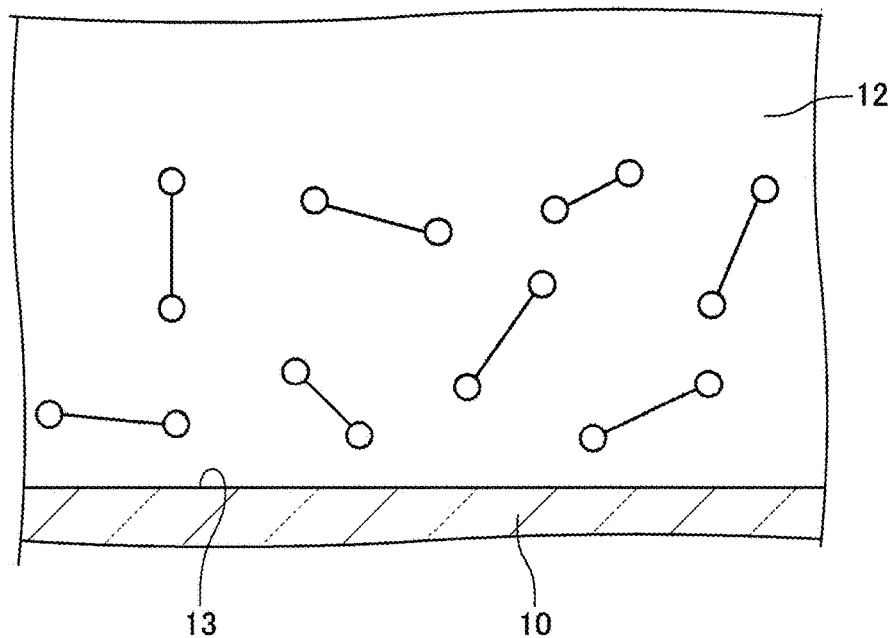
FIG. 10 is a view for illustrating a step of forming a paraffin film according to an embodiment.
Figure 11:
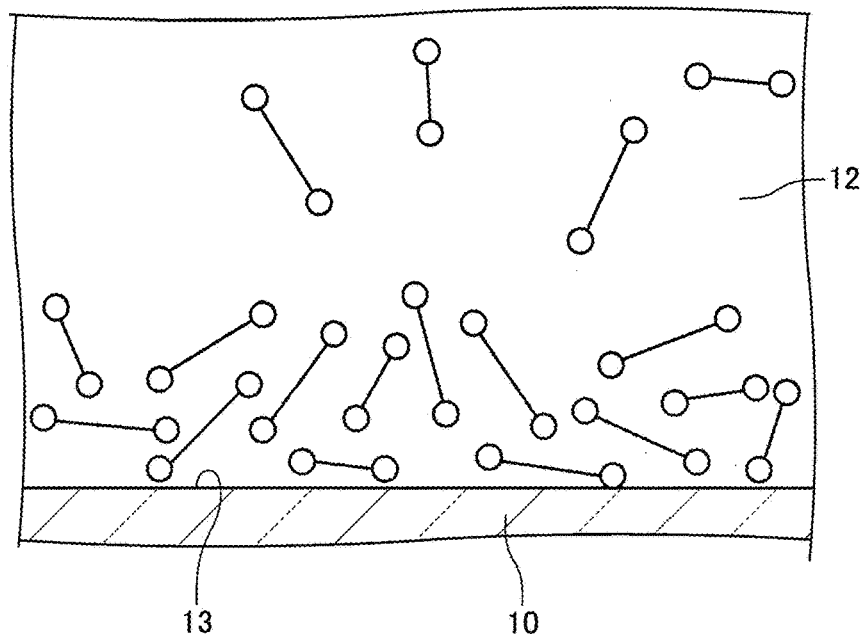
FIG. 11 is a view for illustrating the step of forming a paraffin film according to the embodiment.

As shown in FIG. 9, the coating film 30 is formed on the inner wall 13 of the cell main body 10. Here, with reference to FIG. 10 and FIG. 11, a step of forming the coating film 30 will be described. FIG. 10 and FIG. 11 are views for illustrating the step of forming the coating film 30, and in the same manner as in FIG. 3, a methyl group at both ends of a paraffin is indicated by a circle (◯), and an alkyl chain therebetween is indicated by a segment.

First, in the air, the cell main body 10 is heated, and as shown in FIG. 10, the paraffin stored in the first vessel 50 is vaporized (Step S5, a heating step). The vaporized paraffin is stored in the first chamber 12. In this step, for example, the cell main body 10 is placed on an oven and heated to 200° C. or higher and 500° C. or lower. In this step, the paraffin can be allowed to exist in the first chamber 12 at a saturated vapor pressure. In the case where the amount of the paraffin stored in the first vessel 50 is sufficient, the film thickness of the coating film 30 can be determined by the saturated vapor pressure corresponding to the heating temperature of the cell main body 10.

Subsequently, the cell main body 10 is cooled so as to cool the paraffin to a first temperature higher than the surface freezing temperature (SF temperature) (Step S6, a first cooling step). In this step, the temperature of the cell main body 10 is lowered by, for example, setting the set temperature of the oven having the cell main body 10 placed thereon to a temperature lower than the temperature in the heating step (Step S5). By this step, as shown in FIG. 11, the paraffin which can no longer exist in a gaseous state is adsorbed onto the inner wall 13 so as to be able to form a film in a liquid state. The first temperature is a temperature at which the paraffin which can no longer exist in a gaseous state is adsorbed onto the inner wall 13 so as to be able to form a film in a liquid state. The first temperature is, for example, 100° C. or higher and 200° C. or lower. The temperature lowering rate in this cooling step may be fixed or changed from the heating temperature in the Step S5 to the first temperature. Further, this cooling step may have a part in which the temperature is kept constant. The average temperature lowering rate in this cooling step is, for example, 20° C./hour or more and 40° C./hour or less. The average temperature lowering rate in the cooling step can be represented by (A−B)/T when the temperature is lowered from the initial temperature (A° C.) of the cooling step to the final temperature (B° C.) of the cooling step by taking T hours.

Here, the SF is a phenomenon in which, although the lower layer is a liquid, a solid film is formed only on the surface at a temperature Ts higher than the bulk melting point Tf of the paraffin, and the SF temperature refers to Ts. A difference between the SF temperature Ts of the paraffin and the melting point Tf of the paraffin is, for example, 2° C. or more and 20° C. or less. A difference between the melting point of the paraffin film 34 and the melting point of the paraffin film 32 is, for example, the same as the difference between the SF temperature Ts and the melting point Tf of the paraffin.

Subsequently, the cell main body 10 is cooled so as to cool the paraffin to a second temperature lower than the melting point Tf (Step S7, a second cooling step). In this step, the temperature of the cell main body 10 is lowered by, for example, setting the set temperature of the oven having the cell main body 10 placed thereon to a temperature lower than the melting point Tf. The second temperature is, for example, 50° C. or higher and 150° C. or lower. By this step, the paraffin is solidified into a solid so that the coating film 30 having the paraffin films 32 and 34 can be formed, and the paraffin constituting the paraffin film 34 can be arranged such that the directions in the longitudinal directions of the alkyl chains are aligned. The paraffin films 32 and 34 formed in the heating step (Step S5), the first cooling step (Step S6), and the second cooling step (Step S7) may be pure paraffin films or mixed pure paraffin films. In the case where a plurality of pure paraffin raw materials are used for forming a mixed pure paraffin film, a solid-liquid coexisting region is formed in this step, and a paraffin crystal having a specific composition is deposited in some cases.

The temperature lowering rate in the second cooling step (Step S7) may be fixed or changed from the first temperature to the second temperature. Further, this cooling step may have apart in which the temperature is kept constant. The average temperature lowering rate in this cooling step is, for example, 1° C./hour or more and 10° C./hour or less. The average temperature lowering rate in this cooling step is slower than the average temperature lowering rate by natural cooling (the average temperature lowering rate in the case where the temperature of the paraffin is lowered from the first temperature to the second temperature by natural cooling). The natural cooling refers to cooling in the case where an object to be cooled is left in the air at room temperature (for example, 25° C.) and in a windless environment. The average temperature lowering rate in the second cooling step (Step S7) is slower than the average temperature lowering rate in the first cooling step (Step S6). For example, by setting the temperature lowering rate in the beginning part of the first cooling step fast, and setting the temperature lowering rate in the ending part of the first cooling step slow, the temperature lowering rate in the second cooling step can be more reliably set slower than the temperature lowering rate in the first cooling step.

Subsequently, the paraffin is maintained at the second temperature (Step S8, a maintaining step). For example, by placing the cell main body 10 on the oven at the second temperature for 5 hours or more and 15 hours or less, the coating film 30 having stable properties can be formed.

Subsequently, as shown in FIG. 2, in the first chamber 12 of the cell main body 10, the alkali metal gas 40 is filled (Step S9, a filling step). Specifically, the second vessel 52 having the alkali metal stored therein is destroyed with a laser beam (a case where merely a through-hole is formed is also included), whereby the alkali metal gas 40 is filled in the first chamber 12.

By the above-mentioned steps, the gas cell 100 can be produced.

In the method for producing the gas cell 100, the average temperature lowering rate in the second cooling step (Step S7) is 1° C./hour or more and 10° C./hour or less. In the production of the gas cell 100, the average temperature lowering rate in the second cooling step (Step S7) is 10° C./hour or less, and therefore, the second cooling step in which SF occurs can be performed by taking time, and the paraffin film 34 composed of the paraffin arranged such that the directions in the longitudinal directions of the alkyl chains are aligned can be formed on the surface of the coating film 30. Therefore, in the method for producing the gas cell 100, the gas cell 100 capable of suppressing relaxation of spin polarization can be produced. When the average temperature lowering rate in the second cooling step is faster than 10° C./hour, a region which is not covered with the paraffin arranged such that the directions in the longitudinal directions of the alkyl chains are aligned is generated on the surface of the paraffin film in some cases. Further, in the method for producing the gas cell 100, the average temperature lowering rate in the second cooling step (Step S7) is 1° C./hour or more, and therefore, the production process time can be reduced within a range capable of forming the paraffin film 34 composed of the paraffin arranged such that the directions in the longitudinal directions of the alkyl chains are aligned.

In the method for producing the gas cell 100, a maintaining step of maintaining the paraffin at the second temperature (Step S8) may be included. According to this, in the method for producing the gas cell 100, the paraffin films 32 and 34 having stable properties can be formed.

In the method for producing the gas cell 100, the paraffin films 32 and 34 formed in the heating step (Step S5), the first cooling step (Step S6), and the second cooling step (Step S7) may be mixed pure paraffin films. According to this, in the gas cell 100, the difference between the SF temperature Ts and the melting point Tf of the paraffin can be made larger than in the case where pure paraffin films are formed, and the second cooling step in which SF occurs can be performed by taking time.

In the method for producing the gas cell 100, an alkali metal placing step (Step S3) of placing the second vessel 52 having the alkali metal stored therein in the internal space 18 may be included, and in the filling step (Step S9), the alkali metal gas 40 may be filled in the first chamber 12 by destroying the second vessel 52. According to this, in the method for producing the gas cell 100, in the filling step, the alkali metal gas 40 can be filled in the first chamber 12 in a state where air tightness of the internal space 18 is maintained.

In the method for producing the gas cell 100, the average temperature lowering rate in the second cooling step (Step S7) may be slower than the average temperature lowering rate in the first cooling step (Step S6). According to this, in the method for producing the gas cell 100, the second cooling step in which SF occurs can be performed by taking time, and also by setting the average temperature lowering rate in the first cooling step faster than the average temperature lowering rate in the second cooling step, the production process can be reduced.

Figure 12:
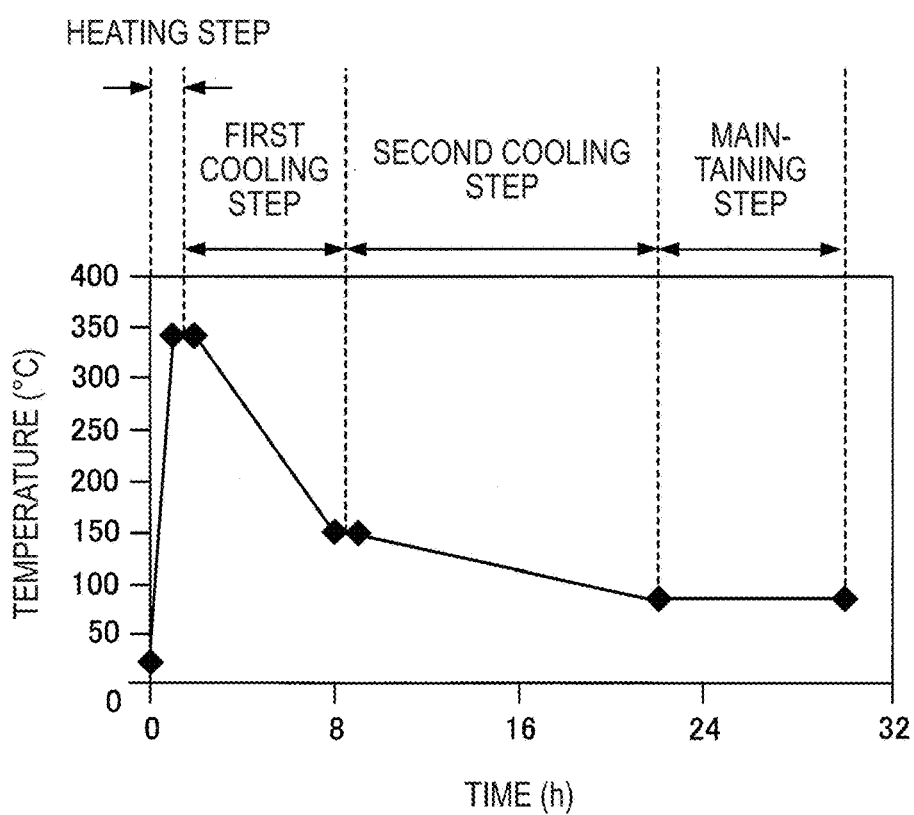
FIG. 12 is a view showing one example of a temperature profile from a heating step to a third cooling step.

Here, FIG. 12 is a view showing one example of a temperature profile (setting value) from the heating step (Step S5) to the third cooling step (Step S8), and is a view showing a profile for forming the coating film 30 composed of pentacontane ($C_{50}H_{102}$). The bulk melting point of pentacontane is about 94° C., and the SF temperature thereof is about 100° C.

In the example shown in FIG. 12, in the heating step, heating to 340° C. is performed, and thereafter, rapid cooling to 150° C. (first temperature) is performed in the first cooling step, and slow cooling to 80° C. (second temperature) is performed in the second cooling step, and then, the temperature is maintained at 80° C. for 8 hours in the third cooling step. In the example shown in FIG. 12, each step is performed by placing the cell main body 10 on the oven.

4. VARIATION OF METHOD FOR PRODUCING GAS CELL

Figure 13:
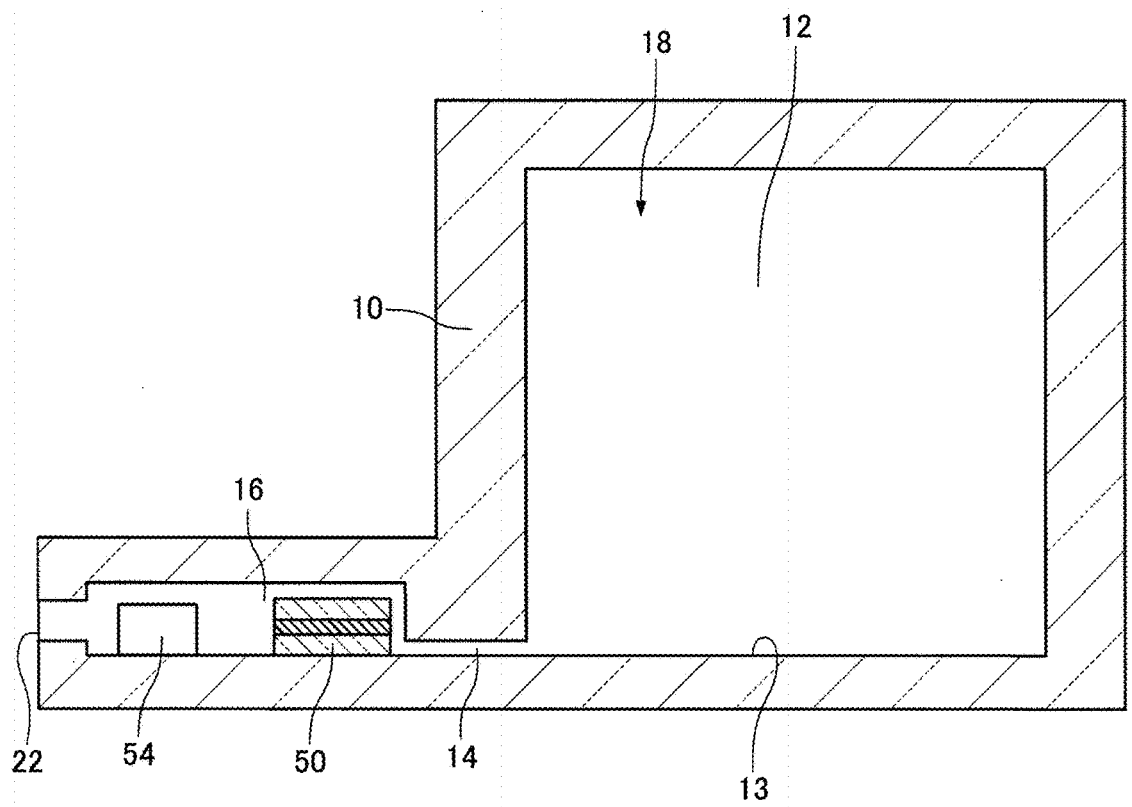
FIG. 13 is a cross-sectional view schematically showing a method for producing a gas cell according to a variation of the embodiment.

Next, a method for producing a gas cell according to a variation of this embodiment will be described with reference to the drawings. FIG. 13 is a cross-sectional view schematically showing a method for producing a gas cell according to a variation of this embodiment. In the method for producing a gas cell according to the variation of this embodiment, different points from the example of the method for producing a gas cell according to this embodiment will be described, and the description of the same points will be omitted.

In the method for producing a gas cell according to the variation of this embodiment, in the alkali metal placing step (Step S3), in place of the second vessel 52 having the alkali metal stored therein, a solid material 54 containing the alkali metal is placed in the internal space 18 as shown in FIG. 13. The solid material 54 is, for example, a pill having a substantially columnar shape. The solid material 54 contains an alkali metal compound and an adsorbent. As the alkali metal compound, in the case where cesium is used as the alkali metal, for example, a cesium compound such as cesium molybdate or cesium chloride is used. As the adsorbent, for example, a zirconium powder, aluminum, or the like is used.

In the method for producing a gas cell according to the variation of this embodiment, in the filling step (Step S9), the alkali metal in a gaseous state is filled in the internal space 18 by irradiating the solid material 54 with a laser beam. By irradiating the solid material 54 with a laser beam, the solid material is heated to activate the alkali metal compound, whereby an alkali metal gas is generated. Impurities or impurity gases released at this time are adsorbed by the adsorbent.

In the method for producing a gas cell according to the variation of this embodiment, the alkali metal gas can be filled in the first chamber 12 without placing the second vessel 52 having the alkali metal stored therein in the internal space 18.

The solid material 54 is not limited to the pill having a substantially columnar shape, and may be, for example, a dispenser having a substantially wire-like shape as long as it can fill the alkali metal in a gaseous state in the internal space 18 by being irradiated with a laser beam.

5. EXPERIMENTAL EXAMPLES

The invention will be more specifically described by showing experimental examples below. The invention is by no means limited to the following experimental examples.

5.1. First Experiment

With respect to two types of gas cells in which the internal space of a cell main body is coated with a pure paraffin film of $C_{50}H_{102}$ or a mixed pure paraffin film of $C_{50}H_{102}$ and $C_{38}H_{78}$, the property of relaxation of spin polarization was evaluated. The pure paraffin film of $C_{50}H_{102}$ is a paraffin film in which a paraffin of $C_{50}H_{102}$ is contained in an amount of 98% or more of the paraffins constituting the paraffin film. The mixed pure paraffin film of $C_{50}H_{102}$ and $C_{38}H_{78}$ is a paraffin film formed by mixing a first pure paraffin raw material containing $C_{50}H_{102}$ in an amount of 98% or more and a second pure paraffin raw material containing $C_{38}H_{78}$ in an amount of 98% or more at 1:9 (the first pure paraffin raw material: the second pure paraffin raw material=1:9). As the alkali metal enclosed in the cell main body, cesium was used.

Figure 14:
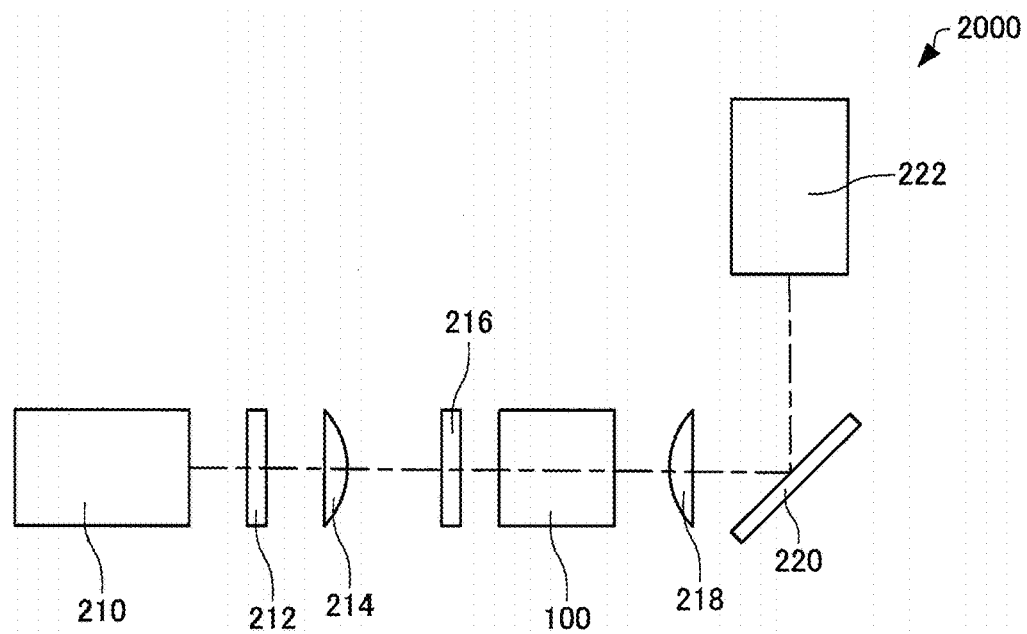
FIG. 14 is a view for illustrating an optical system used in an experimental example.

FIG. 14 is a view for illustrating an optical system 2000 used in this experiment. A light (a laser beam, the wavelength was set to about 894 nm at which the hyperfine structure quantum number of a cesium D1 line shifts from F=4 to F'=3) emitted from a light source 210 was irradiated onto a gas cell 100 through a shutter 212, a lens 214, and a λ/4 wave plate (an element for converting the light into a circularly polarized light) 216. The light transmitted through the gas cell 100 was incident on a photomultiplier tube (detector) 222 through a lens 218 and a mirror 220. For convenience sake, in FIG. 14, the gas cell 100 is shown in a simplified manner. As the optical system 2000 used in this experiment, a document (W. FRANZEN, "Spin Relaxation of Optically Aligned Rubidium Vapor", PHYSICAL REVIEW, Aug. 15, 1959, VOLUME 115, NUMBER 4, pp. 850-856) can be referred to.

In the optical system 2000 described above, after the alkali metal was spin-polarized, the shutter 212 was closed so as to bring the system into a dark state, and a time until spin polarization was relaxed (relaxation in the dark) was measured.

Figure 15:
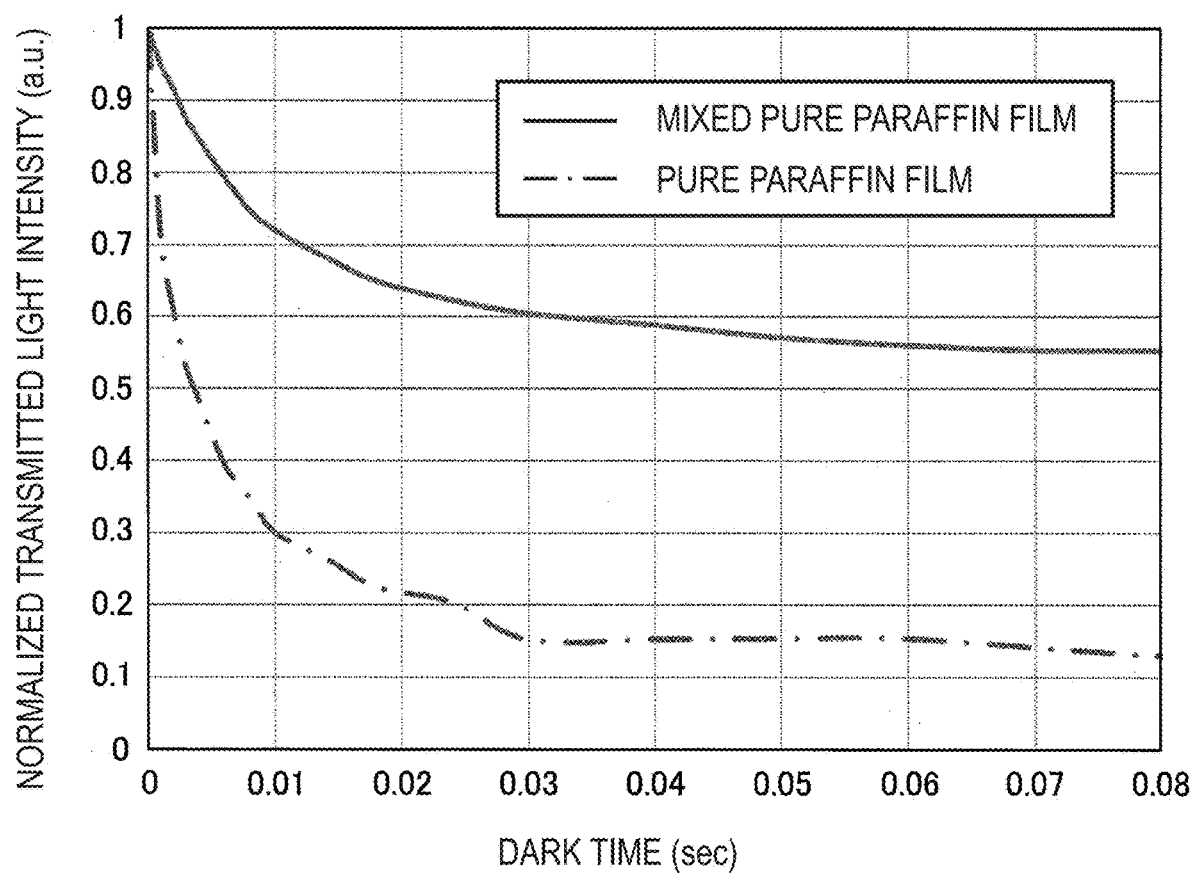
FIG. 15 is a graph showing the results of evaluation of a property of relaxation of spin polarization.

FIG. 15 is a graph showing the results of evaluation of a property of relaxation of spin polarization. In FIG. 15, the horizontal axis represents a time in which the system was in a dark state, and the vertical axis represents a normalized intensity of the light transmitted through the gas cell 100 (a light intensity detected by the photomultiplier tube 222). As the value of the vertical axis is larger, relaxation of spin polarization can be further suppressed.

As shown in FIG. 15, the mixed pure paraffin film had a higher normalized transmission intensity than the pure paraffin film. The relaxation rate in the pure paraffin film was 15.8 Hz. On the other hand, in the mixed pure paraffin film, the relaxation rate was 7.2 Hz, and the relaxation time was longer than in the pure paraffin film. From these results, it was found that the mixed pure paraffin film can suppress relaxation of spin polarization more than the pure paraffin film.

5.2. Second Experiment

A pure paraffin film of $C_{50}H_{102}$ and a mixed pure paraffin film of $C_{50}H_{102}$ and $C_{38}H_{78}$ were observed using a light microscope.

Figure 16:
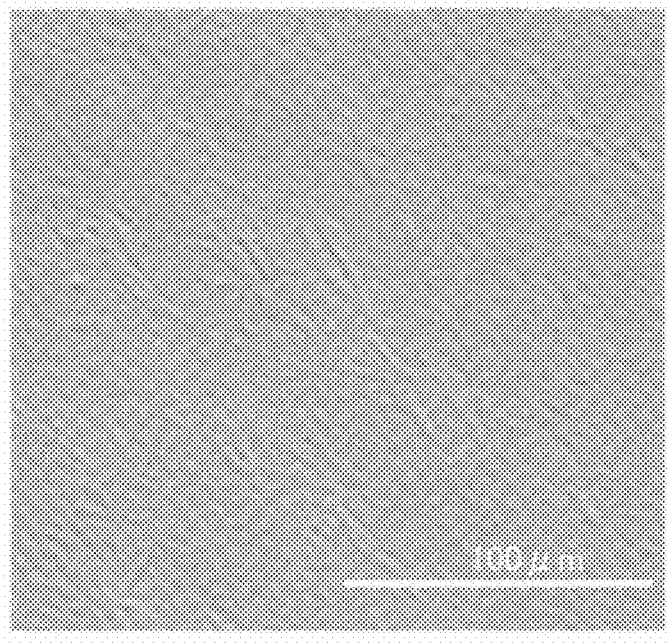
FIG. 16 is a light microscope image.
Figure 17:
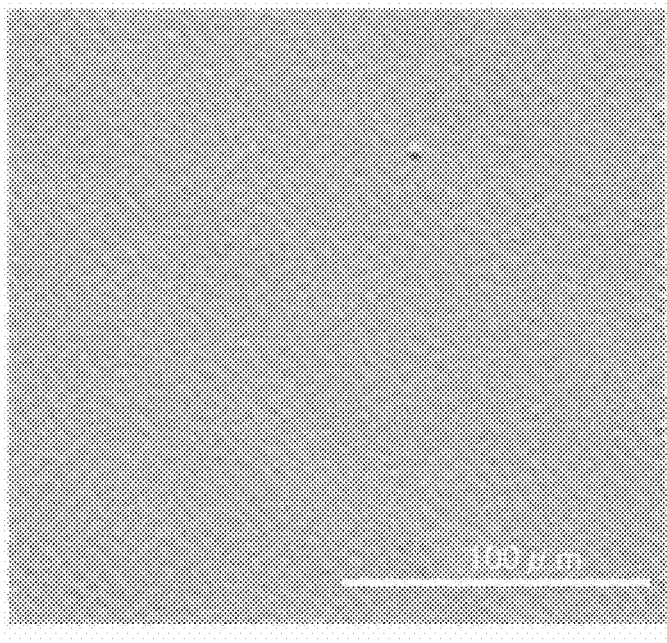
FIG. 17 is a light microscope image.

FIG. 16 is a light microscope image of the pure paraffin film of $C_{50}H_{102}$. FIG. 17 is a light microscope image of the mixed pure paraffin film of $C_{50}H_{102}$ and $C_{38}H_{78}$.

As shown in FIG. 16, on the surface of the pure paraffin film, irregularities were, though slightly, observed. This is presumed to be because microcrystals were formed at a stage of solidification of the lower layer of the pure paraffin film (a portion on the lower side of the pure paraffin film, for example, a portion corresponding to the paraffin film 32 shown in FIG. 3), and thus, irregularities were formed on the surface.

On the other hand, as shown in FIG. 17, irregularities as observed in the pure paraffin film were not observed on the surface of the mixed pure paraffin film, and the surface of the mixed pure paraffin film was smooth. This is presumed to be because in the case of the mixed pure paraffin film, since the lower layer is eutectic or amorphous, grain boundaries of microcrystals or the like were not present in the lower layer, and thus, a smooth surface was maintained.

6. ATOMIC OSCILLATOR

Figure 18:
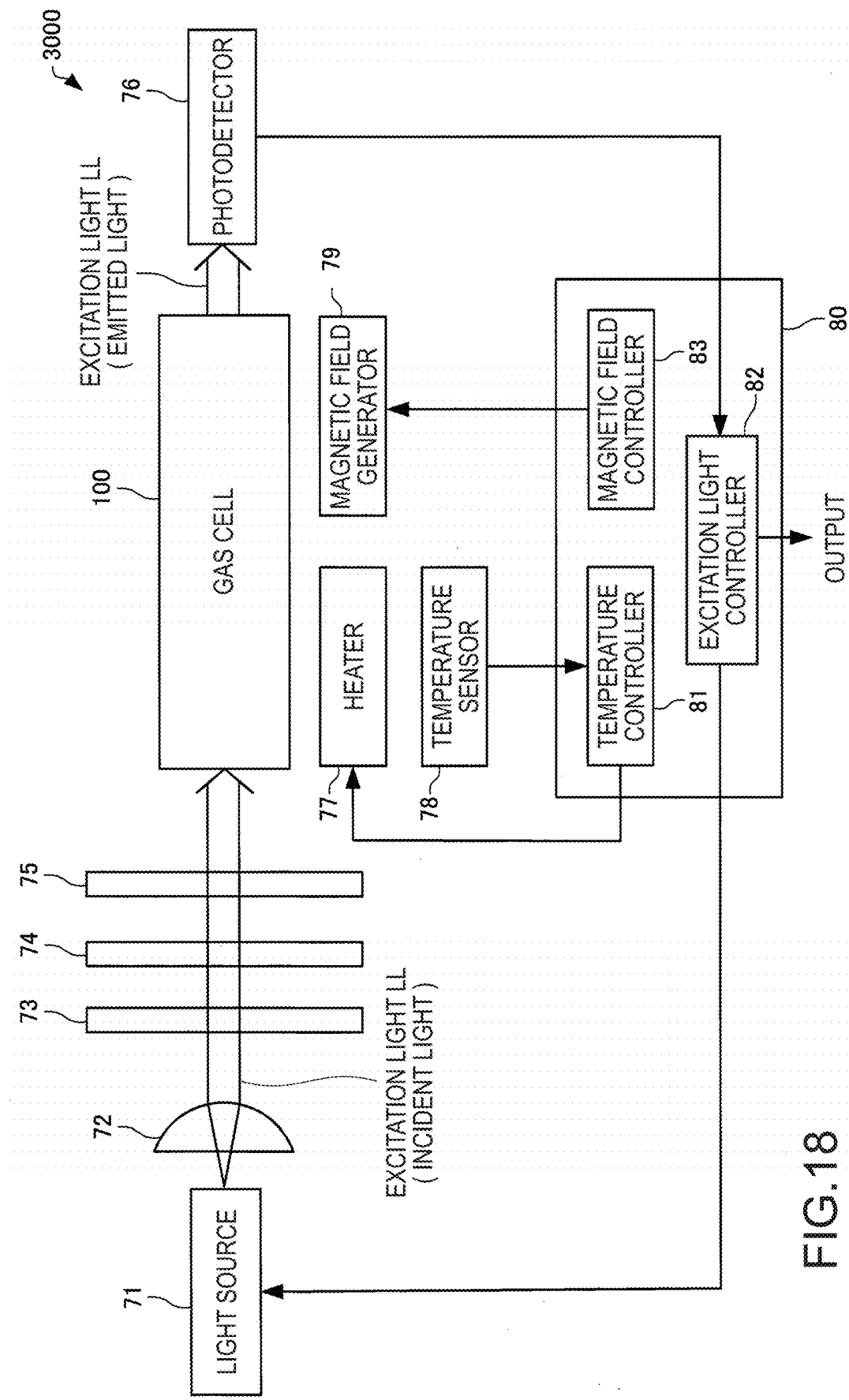
FIG. 18 is a schematic view showing a configuration of an atomic oscillator according to an embodiment.
Figure 19:
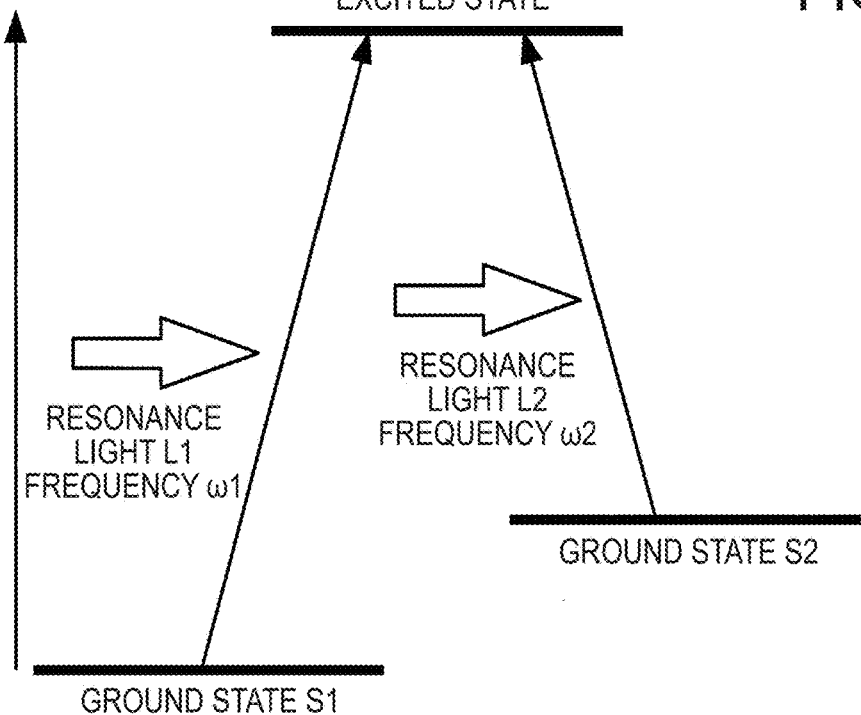
FIG. 19 is a view for illustrating an operation of the atomic oscillator according to the embodiment.
Figure 20:
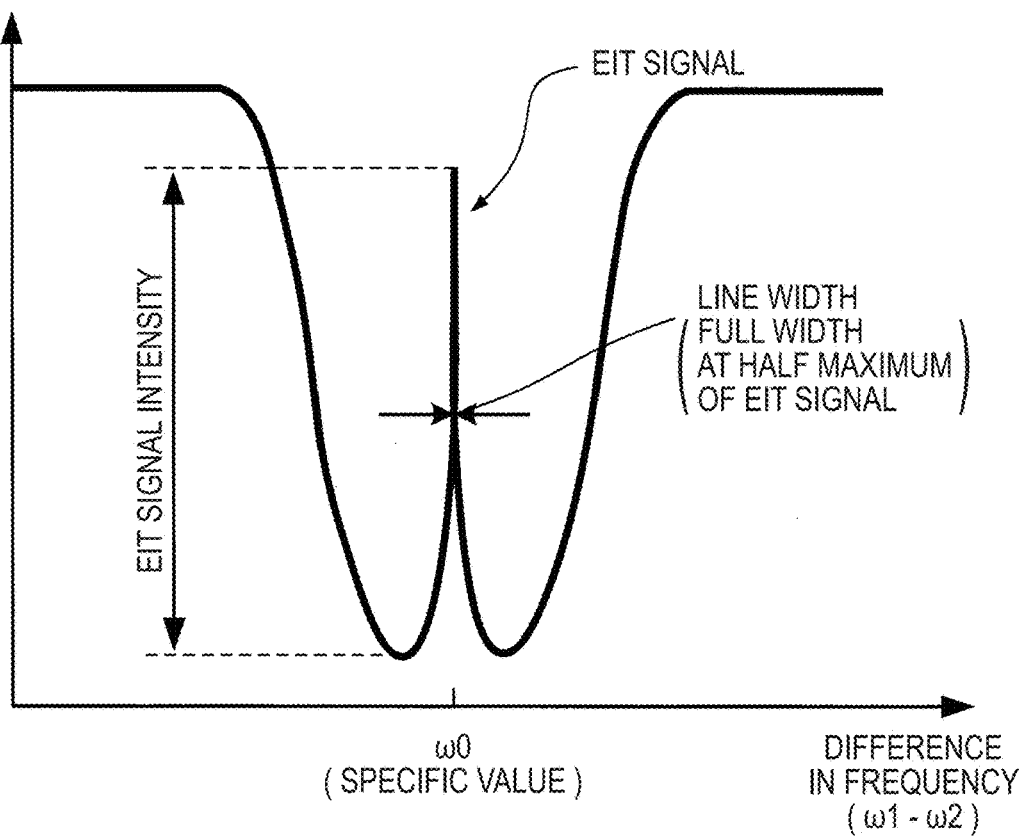
FIG. 20 is a view for illustrating an operation of the atomic oscillator according to the embodiment.

Next, an atomic oscillator according to this embodiment will be described with reference to the drawings. FIG. 18 is a schematic view showing a configuration of anatomic oscillator 3000 according to this embodiment. FIG. 19 and FIG. 20 are views for illustrating an operation of the atomic oscillator 3000 according to this embodiment. The atomic oscillator according to the invention includes the gas cell according to the invention. Hereinafter, the atomic oscillator 3000 including the gas cell 100 described above as the gas cell according to the invention will be described.

The atomic oscillator (quantum interference device) 3000 is an atomic oscillator utilizing a quantum interference effect. As shown in FIG. 18, the atomic oscillator 3000 includes a gas cell 100, a light source 71, optical components 72, 73, 74, and 75, a photodetector 76, a heater 77, a temperature sensor 78, a magnetic field generator 79, and a controller 80.

The light source 71 emits two types of lights (a resonance light L1 and a resonance light L2 shown in FIG. 19) having different frequencies as described below as excitation lights LL which excite alkali metal atoms in the gas cell 100. The light source 71 is constituted by, for example, a semiconductor laser such as a vertical cavity surface emitting laser (VCSEL). The optical components 72, 73, 74, and 75 are each provided on the optical path of the excitation light LL between the light source 71 and the gas cell 100, and the optical component 72 (a lens), the optical component 73 (a polarizing plate), the optical component 74 (a neutral-density filter), and the optical component 75 (a λ/4 wave plate) are placed in this order from the light source 71 side to the gas cell 100 side.

The photodetector 76 detects the intensity of the excitation lights LL (resonance lights L1 and L2) transmitted through the gas cell 100. The photodetector 76 is constituted by, for example, a solar cell, a photodiode, or the like, and is connected to the below-mentioned excitation light controller 82 of the controller 80. The heater 77 (heating section) heats the gas cell 100 for maintaining the alkali metal in the gas cell 100 in a gaseous state (as the alkali metal gas). The heater 77 (heating section) is constituted by, for example, a heating resistor or the like.

The temperature sensor 78 detects the temperature of the heater 77 or the gas cell 100 for controlling the heating value of the heater 77. The temperature sensor 78 is constituted by any of various known temperature sensors such as a thermistor and a thermocouple. The magnetic field generator 79 generates a magnetic field which causes a plurality of degenerate energy levels of the alkali metal in the gas cell 100 to undergo Zeeman splitting. Due to the Zeeman splitting, a gap between the different degenerate energy levels of the alkali metal can be widened, so that the resolution can be improved. As a result, the accuracy of the oscillation frequency of the atomic oscillator 3000 can be enhanced. The magnetic field generator 79 is constituted by, for example, a Helmholtz coil, a solenoid coil, or the like.

The controller 80 includes an excitation light controller 82 which controls the frequencies of the excitation lights LL (resonance lights L1 and L2) emitted from the light source 71, a temperature controller 81 which controls electrical conduction to the heater 77 on the basis of the detection result of the temperature sensor 78, and a magnetic field controller 83 which controls the magnetic field generated from the magnetic field generator 79 to be constant. The controller 80 is provided in, for example, an IC chip mounted on the substrate.

The principle of the atomic oscillator 3000 will be briefly described. FIG. 19 is a view for illustrating the energy state of the alkali metal in the gas cell 100 of the atomic oscillator 3000. FIG. 20 is a graph showing a relationship between a difference in frequency between two lights emitted from the light source 71 and a detection intensity of the photodetector 76 in the atomic oscillator 3000. As shown in FIG. 19, the alkali metal (alkali metal gas) enclosed in the gas cell 100 has energy levels of a three-level system, and can be in the following three states: two ground states (a ground state S1 and a ground state S2) having different energy levels and an excited state. Here, the ground state S1 is a lower energy state than the ground state S2.

When such an alkali metal gas is irradiated with two types of resonance lights L1 and L2 having different frequencies, the light absorption rates (light transmittances) of the resonance lights L1 and L2 in the alkali metal gas 13 change according to a difference ($\omega1-\omega2$) between the frequency $\omega1$ of the resonance light L1 and the frequency $\omega2$ of the resonance light L2. When the difference ($\omega1-\omega2$) between the frequency $\omega1$ of the resonance light L1 and the frequency ω2 of the resonance light L2 matches a frequency corresponding to the difference in energy between the ground state S1 and the ground state S2, excitation from the ground states S1 and S2 to the excited state stops, respectively. At this point, the resonance lights L1 and L2 are both transmitted through the alkali metal without being absorbed by the alkali metal. Such a phenomenon is called a CPT phenomenon or an electromagnetically induced transparency (EIT) phenomenon.

The light source 71 emits two types of lights (the resonance light L1 and the resonance light L2) having different frequencies as described above. Here, for example, when the frequency ω1 of the resonance light L1 is fixed and the frequency ω2 of the resonance light L2 is changed, the detection intensity of the photodetector 76 steeply increases as shown in FIG. 20 when the difference (ω1−ω2) between the frequency ω1 of the resonance light L1 and the frequency ω2 of the resonance light L2 matches a frequency ω0 corresponding to a difference in energy between the ground state S1 and the ground state S2. Such a steep signal is referred to as an EIT signal. The EIT signal has an eigenvalue determined according to the type of alkali metal. Accordingly, by using the EIT signal as a reference, the atomic oscillator 3000 with high accuracy can be realized.

The invention includes substantially the same configurations (for example, configurations having the same functions, methods and results, or configurations having the same objects and effects) as the configurations described in the embodiments. Further, the invention includes configurations in which a part that is not essential in the configurations described in the embodiments is substituted. Further, the invention includes configurations having the same effects as in the configurations described in the embodiments, or configurations capable of achieving the same objects as in the configurations described in the embodiments. In addition, the invention includes configurations in which known techniques are added to the configurations described in the embodiments.

The entire disclosure of Japanese Patent Application No. 2016-226673 filed Nov. 22, 2016 is expressly incorporated by reference herein.

What is claimed is:

1. A gas cell, comprising:
a cell main body having a first chamber defined by an inner wall; and
a first paraffin film provided on the inner wall,
wherein in the first chamber, a gas which interacts with an electromagnetic wave is stored,
the first paraffin film is a pure paraffin film, and
a paraffin constituting the first paraffin film is arranged such that the directions of the molecular axes are aligned.

2. A magnetic field measurement device, comprising the gas cell according to claim 1.

3. The gas cell according to claim 1, wherein a second paraffin film provided between the inner wall and the first paraffin film is included, and
the second paraffin film has a lower melting point than the first paraffin film.

4. A magnetic field measurement device, comprising the gas cell according to claim 3.

5. The gas cell according to claim 1, wherein the gas which interacts with an electromagnetic wave is a gas of an alkali metal.

6. A magnetic field measurement device, comprising the gas cell according to claim 5.

7. The gas cell according to claim 1, wherein the cell main body has a second chamber which communicates with the first chamber through a communication hole.

8. A magnetic field measurement device, comprising the gas cell according to claim 7.

9. A gas cell, comprising:
a cell main body having a first chamber defined by an inner wall; and
a first paraffin film provided on the inner wall,
wherein in the first chamber, a gas which interacts with an electromagnetic wave is stored,
the first paraffin film is a mixed pure paraffin film of a first pure paraffin and a second pure paraffin having a different carbon number from the first paraffin, and
the paraffins constituting the first paraffin film are arranged such that the directions of the molecular axes are aligned.

10. A magnetic field measurement device, comprising the gas cell according to claim 9.

11. The gas cell according to claim 9, wherein the first pure paraffin has a carbon number of 50 and the second pure paraffin has a carbon number of 38.

12. A magnetic field measurement device, comprising the gas cell according to claim 11.

* * * * *